US012605053B2

(12) United States Patent
Bogusky

(10) Patent No.: US 12,605,053 B2
(45) Date of Patent: Apr. 21, 2026

(54) FLEXIBLE ELONGATE DEVICES HAVING AXIAL SUPPORT STRUCTURES

(71) Applicant: INTUITIVE SURGICAL OPERATIONS, INC., Sunnyvale, CA (US)

(72) Inventor: Joseph Bogusky, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 150 days.

(21) Appl. No.: 18/734,439

(22) Filed: Jun. 5, 2024

(65) Prior Publication Data

US 2024/0407635 A1     Dec. 12, 2024

Related U.S. Application Data

(60) Provisional application No. 63/506,660, filed on Jun. 7, 2023.

(51) Int. Cl.
*A61B 1/005*          (2006.01)
(52) U.S. Cl.
CPC ............ *A61B 1/0057* (2013.01); *A61B 1/009* (2022.02)
(58) Field of Classification Search
CPC ..... A61B 1/0055; A61B 1/0057; A61B 1/009; A61B 2034/2061; A61M 25/0147
See application file for complete search history.

(56) References Cited

U.S. PATENT DOCUMENTS

| | | | | |
|---|---|---|---|---|
| 10,863,889 | B2 * | 12/2020 | Schaaf ................... | A61B 1/012 |
| 2005/0131457 | A1 * | 6/2005 | Douglas ................. | A61B 17/29 |
| | | | | 606/205 |
| 2005/0165366 | A1 * | 7/2005 | Brustad ............. | A61M 25/0043 |
| | | | | 604/264 |
| 2006/0149130 | A1 * | 7/2006 | Bob .................... | A61B 1/00154 |
| | | | | 600/114 |
| 2007/0215268 | A1 * | 9/2007 | Pingleton ............ | A61M 25/005 |
| | | | | 156/169 |
| 2007/0233040 | A1 * | 10/2007 | Macnamara ......... | A61B 1/0055 |
| | | | | 604/523 |
| 2007/0233043 | A1 * | 10/2007 | Dayton .............. | A61B 1/00071 |
| | | | | 604/526 |

(Continued)

FOREIGN PATENT DOCUMENTS

| | | | | |
|---|---|---|---|---|
| EP | 1769722 A2 * | 4/2007 | ......... | A61B 1/00133 |

OTHER PUBLICATIONS

"Endoscopic Imaging Technology Today"—Boese et al., Diagnostics 2022, 12, 1262. https://doi.org/10.3390/diagnostics12051262 (Year: 2022).*

(Continued)

*Primary Examiner* — Mainul Hasan
(74) *Attorney, Agent, or Firm* — MARSHALL, GERSTEIN & BORUN LLP

(57)          ABSTRACT
Flexible elongate devices include an elongate body having an articulable body portion and an axial support structure within the articulable body portion. The axial support structure can include a plurality of transverse support segments with tubular struts disposed between the support segments. The flexible elongate devices can include a component line that has a helical shape within the articulable body portion.

23 Claims, 6 Drawing Sheets

(56)  References Cited

U.S. PATENT DOCUMENTS

| | | | |
|---|---|---|---|
| 2008/0208001 A1* | 8/2008 | Hadani | A61B 1/00071 |
| | | | 600/128 |
| 2013/0053772 A1* | 2/2013 | Kappel | A61B 1/005 |
| | | | 604/103.09 |
| 2014/0135576 A1* | 5/2014 | Hebert | A61B 1/05 |
| | | | 600/109 |
| 2016/0270870 A1* | 9/2016 | Kowshik | A61B 34/71 |
| 2017/0095234 A1* | 4/2017 | Prisco | A61B 17/00 |
| 2018/0056040 A1* | 3/2018 | Fenech | A61B 90/37 |
| 2019/0298460 A1* | 10/2019 | Al-Jadda | A61B 1/0057 |
| 2023/0070386 A1* | 3/2023 | Koubi | A61B 1/00105 |
| 2025/0235085 A1* | 7/2025 | Murdeshwar | A61B 1/018 |

OTHER PUBLICATIONS

"Endoscopic Introduction Sheath"—Authors et al.: Disclosed Without Attribution, IP.com Electronic Publication Date: Mar. 6, 2013 (Year: 2013).*

"Variable Stiffness Endoscope Shaft and Articulation Joint and Methods of Making the Same"—Authors et al.: Disclosed Without Attribution, IP.com Electronic Publication Date: Mar. 6, 2013 (Year: 2013).*

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

FLEXIBLE ELONGATE DEVICES HAVING AXIAL SUPPORT STRUCTURES

CROSS-REFERENCE TO RELATED APPLICATION

This application claims the priority benefit of U.S. Provisional Application No. 63/506,660, filed Jun. 7, 2023, which is hereby incorporated by reference herein in its entirety.

FIELD

Disclosed embodiments relate to flexible elongate devices.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions, physicians may insert minimally invasive medical instruments (including surgical, diagnostic, therapeutic, and/or biopsy instruments) to reach a target tissue location. One such minimally invasive technique is to use a flexible and/or steerable elongate device, such as a flexible catheter or endoscope, that can be inserted into anatomic passageways and navigated toward a region of interest within the patient anatomy.

SUMMARY

The following presents a simplified summary of various examples described herein and is not intended to identify key or critical elements or to delineate the scope of the claims.

In accordance with a first example, a flexible elongate device is provided herein that includes an elongate body having an articulable body portion and an axial support structure within the articulable body portion. The axial support structure includes transverse support segments and tubular struts. The transverse support segments are longitudinally spaced along the articulable body portion, where each support segment receives a plurality of pull wires that control articulation of the articulable body portion. The tubular struts are disposed between adjacent support segments, where adjacent tubular struts that are separated by one of the support segments are circumferentially offset relative to one another. Each tubular strut also receives a pull wire therethrough.

In accordance with a second example, a flexible elongate device is provided herein that includes an elongate body comprising an articulable body portion, where the articulable body portion includes an axial support structure and an inner body member within the axial support structure. The flexible elongate device further includes a component line within the axial support structure, where the component line extends in a helical shape around the inner body member. The inner body member has a corkscrew configuration to accommodate the helical shape of the component line within the axial support structure.

It is to be understood that both the foregoing general description and the following detailed description are illustrative and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Figure 1:
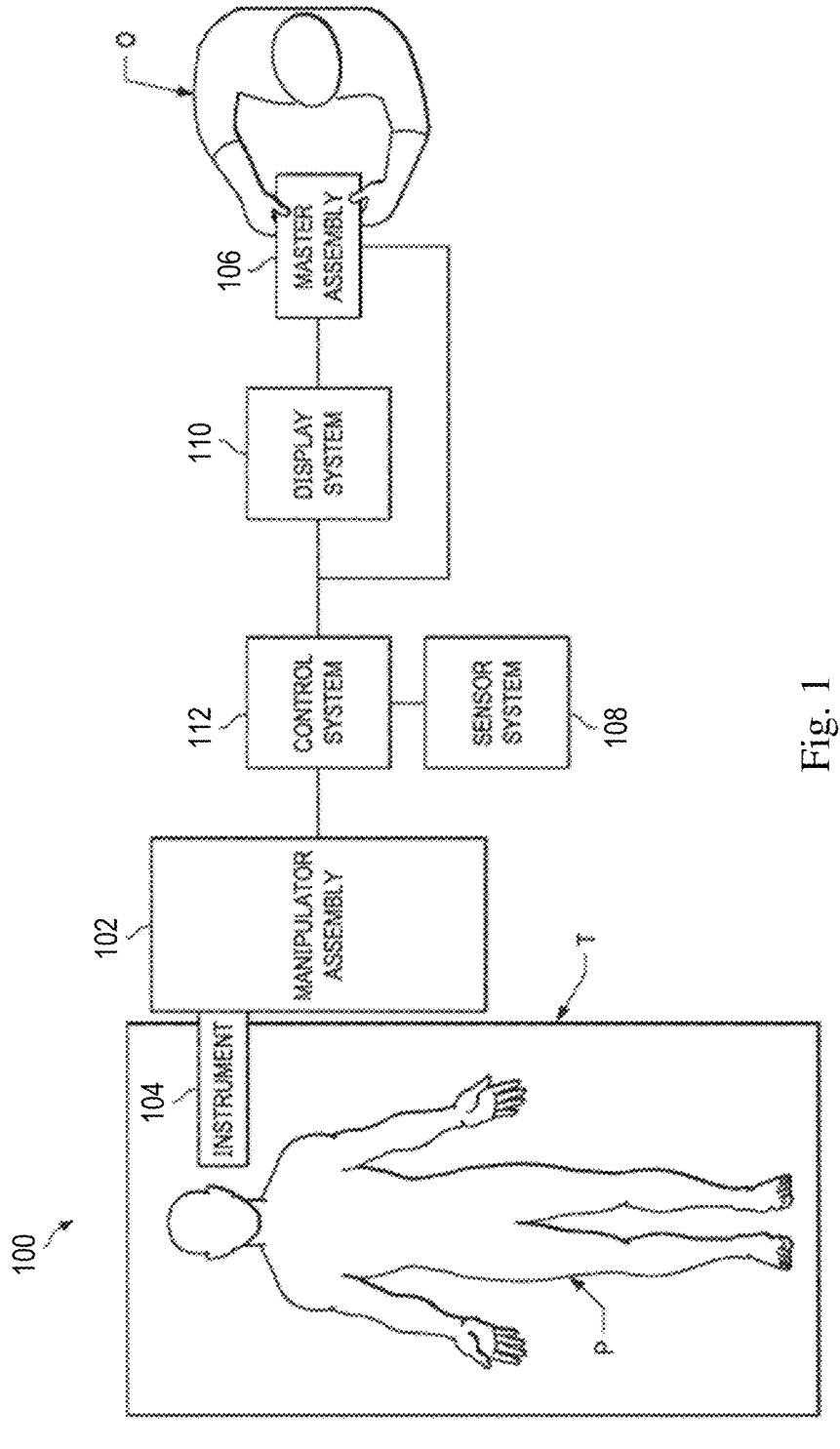
FIG. 1 is a simplified diagram of a medical system according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. In some instances, well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (e.g., one or more degrees of rotational freedom such as, roll, pitch, and yaw). As used herein, the term "pose" refers to the position of an object or a portion of an object in at least one degree of translational freedom and to the orientation of that object or portion of the object in at least one degree of rotational freedom (e.g., up to six total degrees of freedom). As used herein, the term "shape" refers to a set of poses, positions, and/or orientations measured along an object. As used herein, the term "distal" refers to a position that is closer to a procedural site and the term "proximal" refers to a position that is further from the procedural site. Accordingly, the distal portion or distal end of an instrument is closer to a procedural site than a proximal portion or proximal end of the instrument when the instrument is being used as designed to perform a procedure.

Flexible elongate devices that include articulable body portions may include an axial support structure that functions to preserve a neutral axis length for the articulable body portion during articulation thereof, as well as support the articulable body portion against axial loads generated during manipulation of the articulable body portion. For example, the axial support structure may prevent or reduce distortion, compression, and/or collapse of the articulable body portion under axial loads.

Some axial support structures for flexible devices may be formed by cutting away material from a tubular structure. The axial support structures provided herein may have a lower material and manufacturing cost than such axial support structures. The axial support structures also provide improved preservation of the neutral axis length, smaller outer diameter and/or larger working channel, and support for helical wire or sensor integration.

The axial support structures as provided herein include a plurality of support segments that are spaced along a longitudinal axis of the flexible elongate device. The support segments are separated by struts that provide axial stiffness to the axial support structure. Adjacent support segments are separated by at least a pair of struts that are disposed on opposite sides of the support segments, which allows the axial support structure to bend along an axis lateral to the neutral axis relative to the struts. Adjacent pairs of struts are circumferentially offset relative to one another (e.g., a 90 degree offset, a 120 degree offset, etc.) to allow the axial support structure and therefore the articulable body portion to bend along multiple axes (e.g., pitch and yaw).

In some examples, articulation of the articulable body portion of the flexible elongate device can be achieved by manipulation of pull wires coupled to a control structure (e.g., a control ring) disposed within the articulable body portion. The control structure to which the pull wires are attached is distal to the axial support structure and the pull wires pass through the axial support structure to the control structure. In these examples, the support segments can include pull wire openings extending therethrough and the struts may be tubular, such that the pull wires can pass through the plurality of support segments and the struts. The support segments and/or struts may be made from a lubricious material or include a lubricious coating to allow the pull wires to translate/displace therethrough without substantial friction.

In some examples, the flexible elongate device may include an inner body member, which can define a lumen for the flexible elongate device. In these examples, the support segments may have an aperture that is sized to receive the inner body member therethrough. Furthermore, the flexible elongate device may include one or more component lines (e.g., wires, (e.g., shape) sensors, conductors, etc.) that extend within the flexible elongate device between an outer surface of the inner body member and the aperture of the axial support structure. In one embodiment, the apertures of the support segments may be sized to provide sufficient clearance for the component lines regardless of circumferential location (e.g., the difference between the radii of the apertures is greater than or equal to a thickness of the component lines). In another embodiment, the apertures of the support segments may have a diameter sized to provide sufficient clearance for the component lines with the inner body member shifted off-center of the apertures. With this configuration, the inner body member may have a corkscrew configuration, such that the clearances between the apertures of the support segments and inner body member have offsets that provide spaces for the component lines with the component lines wrapped around the inner body member in a helical shape. The helical shape of the component lines may provide benefits for the flexible elongate device, including, for example, a shape sensor providing a volumetric representation of the articulable body portion, and solving the issue of tensile and compressive stress of the component line when they are on the outside of a bend of the articulable body portion. In one example, the support segments are ring shaped with circular apertures, the inner body member has a circular cross section, and the component lines are pass between spaces between the outer surface of the inner body member and the circular apertures of the support segments.

FIG. 1 is a simplified diagram of a medical system 100 according to some embodiments. The medical system 100 may be suitable for use in, for example, surgical, diagnostic (e.g., biopsy), or therapeutic (e.g., ablation, electroporation, etc.) procedures. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems, general or special purpose robotic systems, general or special purpose teleoperational systems, or robotic medical systems.

As shown in FIG. 1, medical system 100 may include a manipulator assembly 102 that controls the operation of a medical instrument 104 in performing various procedures on a patient P. Medical instrument 104 may extend into an internal site within the body of patient P via an opening in the body of patient P. The manipulator assembly 102 may be teleoperated, non-teleoperated, or a hybrid teleoperated and non-teleoperated assembly with one or more degrees of freedom of motion that may be motorized and/or one or more degrees of freedom of motion that may be non-motorized (e.g., manually operated). The manipulator assembly 102 may be mounted to and/or positioned near a patient table T. A master assembly 106 allows an operator O (e.g., a surgeon, a clinician, a physician, or other user) to control the manipulator assembly 102. In some examples, the master assembly 106 allows the operator O to view the procedural site or other graphical or informational displays. In some examples, the manipulator assembly 102 may be excluded from the medical system 100 and the instrument 104 may be controlled directly by the operator O. In some examples, the manipulator assembly 102 may be manually controlled by the operator O. Direct operator control may include various handles and operator interfaces for hand-held operation of the instrument 104.

The master assembly 106 may be located at a surgeon's console which is in proximity to (e.g., in the same room as) a patient table T on which patient P is located, such as at the side of the patient table T. In some examples, the master assembly 106 is remote from the patient table T, such as in in a different room or a different building from the patient table T. The master assembly 106 may include one or more control devices for controlling the manipulator assembly 102. The control devices may include any number of a variety of input devices, such as joysticks, trackballs, scroll wheels, directional pads, buttons, data gloves, trigger-guns, hand-operated controllers, voice recognition devices, motion or presence sensors, and/or the like.

The manipulator assembly 102 supports the medical instrument 104 and may include a kinematic structure of links that provide a set-up structure. The links may include one or more non-servo controlled links (e.g., one or more links that may be manually positioned and locked in place) and/or one or more servo controlled links (e.g., one or more links that may be controlled in response to commands, such as from a control system 112). The manipulator assembly 102 may include a plurality of actuators (e.g., motors) that drive inputs on the medical instrument 104 in response to commands, such as from the control system 112. The actuators may include drive systems that move the medical instrument 104 in various ways when coupled to the medical instrument 104. For example, one or more actuators may advance medical instrument 104 into a naturally or surgically created anatomic orifice. Actuators may control articulation of the medical instrument 104, such as by moving the distal end (or any other portion) of medical instrument 104 in multiple degrees of freedom. These degrees of freedom may include three degrees of linear motion (e.g., linear motion along the X, Y, Z Cartesian axes) and in three degrees of rotational motion (e.g., rotation about the X, Y, Z Cartesian axes). One or more actuators may control rotation of the medical instrument about a longitudinal axis. Actuators can also be used to move an articulable end effector of medical instrument 104, such as for grasping tissue in the jaws of a biopsy device and/or the like, or may be used to move or otherwise control tools (e.g., imaging tools, ablation tools, biopsy tools, electroporation tools, etc.) that are inserted within the medical instrument 104.

The medical system 100 may include a sensor system 108 with one or more sub-systems for receiving information about the manipulator assembly 102 and/or the medical instrument 104. Such sub-systems may include a position sensor system (e.g., that uses electromagnetic (EM) sensors or other types of sensors that detect position or location); a shape sensor system for determining the position, orientation, speed, velocity, pose, and/or shape of a distal end and/or of one or more segments along a flexible body of the medical instrument 104; a visualization system (e.g., using a color imaging device, an infrared imaging device, an ultrasound imaging device, an x-ray imaging device, a fluoroscopic imaging device, a computed tomography (CT) imaging device, a magnetic resonance imaging (MRI) imaging device, or some other type of imaging device) for capturing images, such as from the distal end of medical instrument 104 or from some other location; and/or actuator position sensors such as resolvers, encoders, potentiometers, and the like that describe the rotation and/or orientation of the actuators controlling the medical instrument 104.

The medical system 100 may include a display system 110 for displaying an image or representation of the proce-dural site and the medical instrument 104. Display system 110 and master assembly 106 may be oriented so physician O can control medical instrument 104 and master assembly 106 with the perception of telepresence.

In some embodiments, the medical instrument 104 may include a visualization system, which may include an image capture assembly that records a concurrent or real-time image of a procedural site and provides the image to the operator O through one or more displays of display system 110. The image capture assembly may include various types of imaging devices. The concurrent image may be, for example, a two-dimensional image or a three-dimensional image captured by an endoscope positioned within the anatomical procedural site. In some examples, the visualization system may include endoscopic components that may be integrally or removably coupled to medical instrument 104. Additionally or alternatively, a separate endoscope, attached to a separate manipulator assembly, may be used with medical instrument 104 to image the procedural site. The visualization system may be implemented as hardware, firmware, software or a combination thereof which interact with or are otherwise executed by one or more computer processors, such as of the control system 112.

Display system 110 may also display an image of the procedural site and medical instruments, which may be captured by the visualization system. In some examples, the medical system 100 provides a perception of telepresence to the operator O. For example, images captured by an imaging device at a distal portion of the medical instrument 104 may be presented by the display system 110 to provide the perception of being at the distal portion of the medical instrument 104 to the operator O. The input to the master assembly 106 provided by the operator O may move the distal portion of the medical instrument 104 in a manner that corresponds with the nature of the input (e.g., distal tip turns right when a trackball is rolled to the right) and results in corresponding change to the perspective of the images captured by the imaging device at the distal portion of the medical instrument 104. As such, the perception of telepresence for the operator O is maintained as the medical instrument 104 is moved using the master assembly 106. The operator O can manipulate the medical instrument 104 and hand controls of the master assembly 106 as if viewing the workspace in substantially true presence, simulating the experience of an operator that is physically manipulating the medical instrument 104 from within the patient anatomy.

In some examples, the display system 110 may present virtual images of a procedural site that are created using image data recorded pre-operatively (e.g., prior to the procedure performed by the medical instrument system 200) or intra-operatively (e.g., concurrent with the procedure performed by the medical instrument system 200), such as image data created using computed tomography (CT), magnetic resonance imaging (MRI), positron emission tomography (PET), fluoroscopy, thermography, ultrasound, optical coherence tomography (OCT), thermal imaging, impedance imaging, laser imaging, nanotube X-ray imaging, and/or the like. The virtual images may include two-dimensional, three-dimensional, or higher-dimensional (e.g., including, for example, time based or velocity-based information) images. In some examples, one or more models are created from pre-operative or intra-operative image data sets and the virtual images are generated using the one or more models.

In some examples, for purposes of imaged guided medical procedures, display system 110 may display a virtual image that is generated based on tracking the location of medical instrument 104. For example, the tracked location of the medical instrument 104 may be registered (e.g., dynamically referenced) with the model generated using the pre-operative or intra-operative images, with different portions of the model correspond with different locations of the patient anatomy. As the medical instrument 104 moves through the patient anatomy, the registration is used to determine portions of the model corresponding with the location and/or perspective of the medical instrument 104 and virtual images are generated using the determined portions of the model. This may be done to present the operator O with virtual images of the internal procedural site from viewpoints of medical instrument 104 that correspond with the tracked locations of the medical instrument 104.

The medical system 100 may also include the control system 112, which may include processing circuitry that implements the some or all of the methods or functionality discussed herein. The control system 112 may include at least one memory and at least one processor for controlling the operations of the manipulator assembly 102, the medical instrument 104, the master assembly 106, the sensor system 108, and/or the display system 110. Control system 112 may include instructions (e.g., a non-transitory machine-readable medium storing the instructions) that when executed by the at least one processor, configures the one or more processors to implement some or all of the methods or functionality discussed herein. While the control system 112 is shown as a single block in FIG. 1, the control system 112 may include two or more separate data processing circuits with one portion of the processing being performed at the manipulator assembly 102, another portion of the processing being performed at the master assembly 106, and/or the like. In some examples, the control system 112 may include other types of processing circuitry, such as application-specific integrated circuits (ASICs) and/or field-programmable gate array (FPGAs). The control system 112 may be implemented using hardware, firmware, software, or a combination thereof.

In some examples, the control system 112 may receive feedback from the medical instrument 104, such as force and/or torque feedback. Responsive to the feedback, the control system 112 may transmit signals to the master assembly 106. In some examples, the control system 112 may transmit signals instructing one or more actuators of the manipulator assembly 102 to move the medical instrument 104. In some examples, the control system 112 may transmit informational displays regarding the feedback to the display system 110 for presentation or perform other types of actions based on the feedback.

The control system 112 may include a virtual visualization system to provide navigation assistance to operator O when controlling the medical instrument 104 during an image-guided medical procedure. Virtual navigation using the virtual visualization system may be based upon an acquired pre-operative or intra-operative dataset of anatomic passageways of the patient P. The control system 112 or a separate computing device may convert the recorded images, using programmed instructions alone or in combination with operator inputs, into a model of the patient anatomy. The model may include a segmented two-dimensional or three-dimensional composite representation of a partial or an entire anatomic organ or anatomic region. An image data set may be associated with the composite representation. The virtual visualization system may obtain sensor data from the sensor system 108 that is used to compute an (e.g., approximate) location of the medical instrument 104 with respect to the anatomy of patient P. The sensor system 108 may be used to register and display the medical instrument 104 together with the pre-operatively or intra-operatively recorded images. For example, PCT Publication WO 2016/191298 (published Dec. 1, 2016 and titled "Systems and Methods of Registration for Image Guided Surgery"), which is incorporated by reference herein in its entirety, discloses example systems.

During a virtual navigation procedure, the sensor system 108 may be used to compute the (e.g., approximate) location of the medical instrument 104 with respect to the anatomy of patient P. The location can be used to produce both macro-level (e.g., external) tracking images of the anatomy of patient P and virtual internal images of the anatomy of patient P. The system may include one or more electromagnetic (EM) sensors, fiber optic sensors, and/or other sensors to register and display a medical instrument together with pre-operatively recorded medical images. For example, U.S. Pat. No. 8,900,131 (filed May 13, 2011 and titled "Medical System Providing Dynamic Registration of a Model of an Anatomic Structure for Image-Guided Surgery"), which is incorporated by reference herein in its entirety, discloses example systems.

Medical system 100 may further include operations and support systems (not shown) such as illumination systems, steering control systems, irrigation systems, and/or suction systems. In some embodiments, the medical system 100 may include more than one manipulator assembly and/or more than one master assembly. The exact number of manipulator assemblies may depend on the medical procedure and space constraints within the procedural room, among other factors. Multiple master assemblies may be co-located or they may be positioned in separate locations. Multiple master assemblies may allow more than one operator to control one or more manipulator assemblies in various combinations.

Figures 2A, 2B:
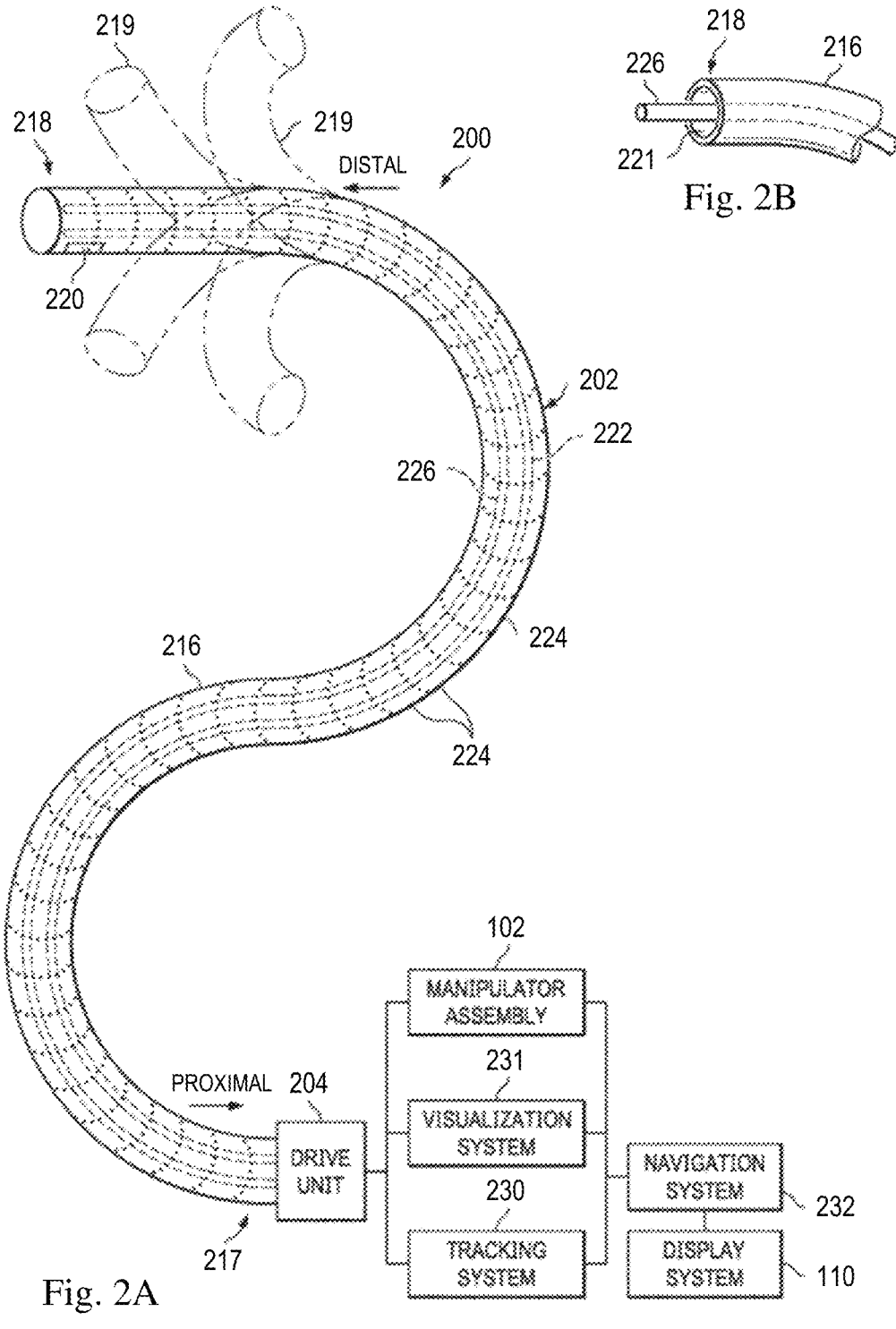
FIG. 2A is a simplified diagram of a medical instrument system according to some embodiments.
FIG. 2B is a simplified diagram of a medical instrument including a medical tool within an elongate device according to some embodiments.

FIG. 2A is a simplified diagram of a medical instrument system 200 according to some embodiments. The medical instrument system 200 includes a flexible elongate device 202 (also referred to as elongate device 202), a drive unit 204, and a medical tool 226 that collectively is an example of a medical instrument 104 of a medical system 100. The medical system 100 may be a teleoperated system, a non-teleoperated system, or a hybrid teleoperated and non-teleoperated system, as explained with reference to FIG. 1. A visualization system 231, tracking system 230, and navigation system 232 are also shown in FIG. 2A and are example components of the control system 112 of the medical system 100. In some examples, the medical instrument system 200 may be used for non-teleoperational exploratory procedures or in procedures involving traditional manually operated medical instruments, such as endoscopy. The medical instrument system 200 may be used to gather (e.g., measure) a set of data points corresponding to locations within anatomic passageways of a patient, such as patient P.

The elongate device 202 is coupled to the drive unit 204. The elongate device 202 includes a channel 221 through which the medical tool 226 may be inserted. The elongate device 202 navigates within patient anatomy to deliver the medical tool 226 to a procedural site. The elongate device 202 includes a flexible body 216 having a proximal end 217 and a distal end 218. In some examples, the flexible body 216 may have an approximately 3 mm outer diameter. Other flexible body outer diameters may be larger or smaller.

Medical instrument system 200 may include the tracking system 230 for determining the position, orientation, speed, velocity, pose, and/or shape of the flexible body 216 at the distal end 218 and/or of one or more segments 224 along flexible body 216, as will be described in further detail below. The tracking system 230 may include one or more sensors and/or imaging devices. The flexible body 216, such as the length between the distal end 218 and the proximal end 217, may include multiple segments 224. The tracking system 230 may be implemented using hardware, firmware, software, or a combination thereof. In some examples, the tracking system 230 is part of control system 112 shown in FIG. 1.

Tracking system 230 may track the distal end 218 and/or one or more of the segments 224 of the flexible body 216 using a shape sensor 222. The shape sensor 222 may include an optical fiber aligned with the flexible body 216 (e.g., provided within an interior channel of the flexibly body 216 or mounted externally along the flexible body 216). In some examples, the optical fiber may have a diameter of approximately 200 µm. In other examples, the diameter may be larger or smaller. The optical fiber of the shape sensor 222 may form a fiber optic bend sensor for determining the shape of flexible body 216. Optical fibers including Fiber Bragg Gratings (FBGs) may be used to provide strain measurements in structures in one or more dimensions. Various systems and methods for monitoring the shape and relative position of an optical fiber in three dimensions, which may be applicable in some embodiments, are described in U.S. Patent Application Publication No. 2006/0013523 (filed Jul. 13, 2005 and titled "Fiber optic position and shape sensing device and method relating thereto"); U.S. Pat. No. 7,772, 541 (filed on Mar. 12, 2008 and titled "Fiber Optic Position and/or Shape Sensing Based on Rayleigh Scatter"); and U.S. Pat. No. 8,773,650 (filed on Sep. 2, 2010 and titled "Optical Position and/or Shape Sensing"), which are all incorporated by reference herein in their entireties. Sensors in some embodiments may employ other suitable strain sensing techniques, such as Rayleigh scattering, Raman scattering, Brillouin scattering, and Fluorescence scattering.

In some examples, the shape of the flexible body 216 may be determined using other techniques. For example, a history of the position and/or pose of the distal end 218 of the flexible body 216 can be used to reconstruct the shape of flexible body 216 over an interval of time (e.g., as the flexible body 216 is advanced or retracted within a patient anatomy). In some examples, the tracking system 230 may alternatively and/or additionally track the distal end 218 of the flexible body 216 using a position sensor system 220. Position sensor system 220 may be a component of an EM sensor system with the position sensor system 220 including one or more position sensors. Although the position sensor system 220 is shown as being near the distal end 218 of the flexible body 216 to track the distal end 218, the number and location of the position sensors of the position sensor system 220 may vary to track different regions along the flexible body 216. In one example, the position sensors include conductive coils that may be subjected to an externally generated electromagnetic field. Each coil of position sensor system 220 may produce an induced electrical signal having characteristics that depend on the position and orientation of the coil relative to the externally generated electromagnetic field. The position sensor system 220 may measure one or more position coordinates and/or one or more orientation angles associated with one or more portions of flexible body 216. In some examples, the position sensor system 220 may be configured and positioned to measure six degrees of freedom, e.g., three position coordinates X, Y, Z and three orientation angles indicating pitch, yaw, and roll of a base point. In some examples, the position sensor system 220 may be configured and positioned to measure five degrees of freedom, e.g., three position coordinates X, Y, Z and two orientation angles indicating pitch and yaw of a base point. Further description of a position sensor system, which may be applicable in some embodiments, is provided in U.S. Pat. No. 6,380,732 (filed Aug. 11, 1999 and titled "Six-Degree of Freedom Tracking System Having a Passive Transponder on the Object Being Tracked"), which is incorporated by reference herein in its entirety.

In some embodiments, the tracking system 230 may alternately and/or additionally rely on a collection of pose, position, and/or orientation data stored for a point of an elongate device 202 and/or medical tool 226 captured during one or more cycles of alternating motion, such as breathing. This stored data may be used to develop shape information about the flexible body 216. In some examples, a series of position sensors (not shown), such as EM sensors like the sensors in position sensor 220 or some other type of position sensors may be positioned along the flexible body 216 and used for shape sensing. In some examples, a history of data from one or more of these position sensors taken during a procedure may be used to represent the shape of elongate device 202, particularly if an anatomic passageway is generally static.

FIG. 2B is a simplified diagram of the medical tool 226 within the elongate device 202 according to some embodiments. The flexible body 216 of the elongate device 202 may include the channel 221 sized and shaped to receive the medical tool 226. In some embodiments, the medical tool 226 may be used for procedures such as diagnostics, imaging, surgery, biopsy, ablation, illumination, irrigation, suction, electroporation, etc. Medical tool 226 can be deployed through channel 221 of flexible body 216 and operated at a procedural site within the anatomy. Medical instrument 226 may be, for example, an image capture probe, a biopsy tool (e.g., a needle, grasper, brush, etc.), an ablation tool (e.g., a laser ablation tool, radio frequency (RF) ablation tool, cryoablation tool, thermal ablation tool, heated liquid ablation tool, etc.), an electroporation tool, and/or another surgical, diagnostic, or therapeutic tool. In some examples, the medical tool 226 may include an end effector having a single working member such as a scalpel, a blunt blade, an optical fiber, an electrode, and/or the like. Other end types of end effectors may include, for example, forceps, graspers, scissors, staplers, clip appliers, and/or the like. Other end effectors may further include electrically activated end effectors such as electrosurgical electrodes, transducers, sensors, and/or the like.

The medical tool 226 may be a biopsy tool used to remove sample tissue or a sampling of cells from a target anatomic location. In some examples, the biopsy tool is a flexible needle. The biopsy tool may further include a sheath that can surround the flexible needle to protect the needle and interior surface of the channel 221 when the biopsy tool is within the channel 221. The medical tool 226 may be an image capture probe that includes a distal portion with a stereoscopic or monoscopic camera that may be placed at or near the distal end 218 of flexible body 216 for capturing images (e.g., still or video images). The captured images may be processed by the visualization system 231 for display and/or provided to the tracking system 230 to support tracking of the distal end 218 of the flexible body 216 and/or one or more of the segments 224 of the flexible body 216. The image capture probe may include a cable for transmitting the captured image data that is coupled to an imaging device at the distal portion of the image capture probe. In some examples, the image capture probe may include a fiber-optic bundle, such as a fiberscope, that couples to a more proximal imaging device of the visualization system 231. The image capture probe may be single-spectral or multi-spectral, for example, capturing image data in one or more of the visible, near-infrared, infrared, and/or ultraviolet spectrums. The image capture probe may also include one or more light emitters that provide illumination to facilitate image capture. In some examples, the image capture probe may use ultrasound, x-ray, fluoroscopy, CT, MRI, or other types of imaging technology.

In some examples, the image capture probe is inserted within the flexible body 216 of the elongate device 202 to facilitate visual navigation of the elongate device 202 to a procedural site and then is replaced within the flexible body 216 with another type of medical tool 226 that performs the procedure. In some examples, the image capture probe may be within the flexible body 216 of the elongate device 202 along with another type of medical tool 226 to facilitate simultaneous image capture and tissue intervention, such as within the same channel 221 or in separate channels. A medical tool 226 may be advanced from the opening of the channel 221 to perform the procedure (or some other functionality) and then retracted back into the channel 221 when the procedure is complete. The medical tool 226 may be removed from the proximal end 217 of the flexible body 216 or from another optional instrument port (not shown) along flexible body 216.

In some examples, the elongate device 202 may include integrated imaging capability rather than utilize a removable image capture probe. For example, the imaging device (or fiber-optic bundle) and the light emitters may be located at the distal end 218 of the elongate device 202. The flexible body 215 may include one or more dedicated channels that carry the cable(s) and/or optical fiber(s) between the distal end 218 and the visualization system 231. Here, the medical instrument system 200 can perform simultaneous imaging and tool operations.

In some examples, the medical tool 226 is capable of controllable articulation. The medical tool 226 may house cables (which may also be referred to as pull wires), linkages, or other actuation controls (not shown) that extend between its proximal and distal ends to controllably bend the distal end of medical tool 226, such as discussed herein for the flexible elongate device 202. The medical tool 226 may be coupled to a drive unit 204 and the manipulator assembly 102. In these examples, the elongate device 202 may be excluded from the medical instrument system 200 or may be a flexible device that does not have controllable articulation. Steerable instruments or tools, applicable in some embodiments, are further described in detail in U.S. Pat. No. 7,316,681 (filed on Oct. 4, 2005 and titled "Articulated Surgical Instrument for Performing Minimally Invasive Surgery with Enhanced Dexterity and Sensitivity") and U.S. Pat. No. 9,259,274 (filed Sep. 30, 2008 and titled "Passive Preload and Capstan Drive for Surgical Instruments"), which are incorporated by reference herein in their entireties.

The flexible body 216 of the elongate device 202 may also or alternatively house cables, linkages, or other steering controls (not shown) that extend between the drive unit 204 and the distal end 218 to controllably bend the distal end 218 as shown, for example, by broken dashed line depictions 219 of the distal end 218 in FIG. 2A. In some examples, at least four cables are used to provide independent up-down steering to control a pitch of the distal end 218 and left-right steering to control a yaw of the distal end 281. In these examples, the flexible elongate device 202 may be a steerable catheter. Examples of steerable catheters, applicable in some embodiments, are described in detail in PCT Publication WO 2019/018736 (published Jan. 24, 2019 and titled "Flexible Elongate Device Systems and Methods"), which is incorporated by reference herein in its entirety.

In embodiments where the elongate device 202 and/or medical tool 226 are actuated by a teleoperational assembly (e.g., the manipulator assembly 102), the drive unit 204 may include drive inputs that removably couple to and receive power from drive elements, such as actuators, of the teleoperational assembly. In some examples, the elongate device 202 and/or medical tool 226 may include gripping features, manual actuators, or other components for manually controlling the motion of the elongate device 202 and/or medical tool 226. The elongate device 202 may be steerable or, alternatively, the elongate device 202 may be non-steerable with no integrated mechanism for operator control of the bending of distal end 218. In some examples, one or more channels 221 (which may also be referred to as lumens), through which medical tools 226 can be deployed and used at a target anatomical location, may be defined by the interior walls of the flexible body 216 of the elongate device 202.

In some examples, the medical instrument system 200 (e.g., the elongate device 202 or medical tool 226) may include a flexible bronchial instrument, such as a bronchoscope or bronchial catheter, for use in examination, diagnosis, biopsy, and/or treatment of a lung. The medical instrument system 200 may also be suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from the tracking system 230 may be sent to the navigation system 232, where the information may be combined with information from the visualization system 231 and/or pre-operatively obtained models to provide the physician, clinician, surgeon, or other operator with real-time position information. In some examples, the real-time position information may be displayed on the display system 110 for use in the control of the medical instrument system 200. In some examples, the navigation system 232 may utilize the position information as feedback for positioning medical instrument system 200. Various systems for using fiber optic sensors to register and display a surgical instrument with surgical images, applicable in some embodiments, are provided in U.S. Pat. No. 8,900,131 (filed May 13, 2011 and titled "Medical System Providing Dynamic Registration of a Model of an Anatomic Structure for Image-Guided Surgery"), which is incorporated by reference herein in its entirety.

Figure 3A:
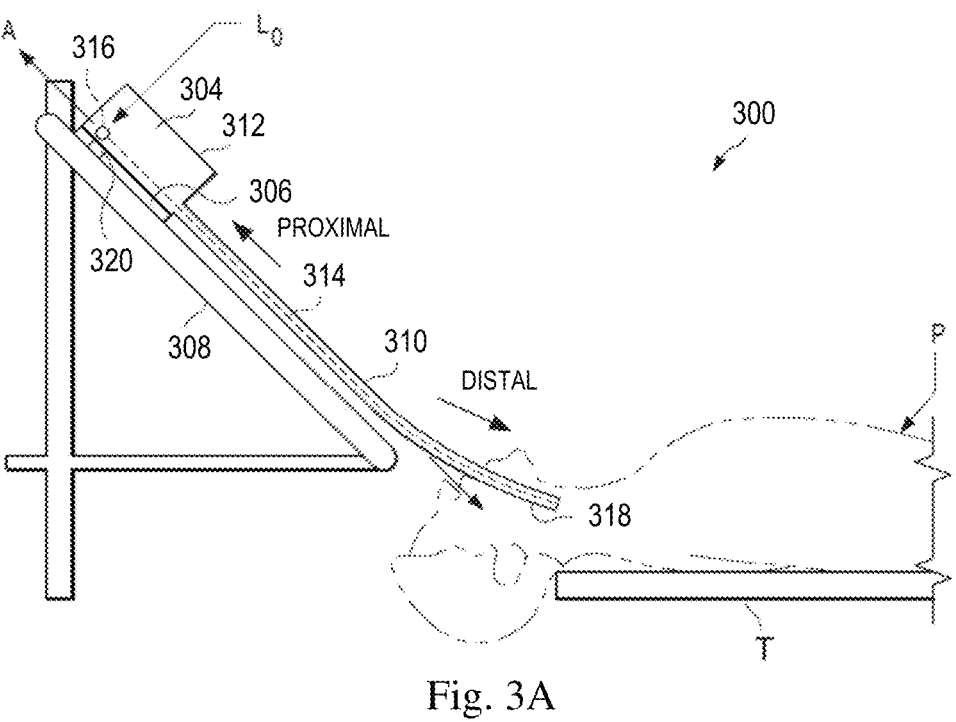
FIGS. 3A and 3B are simplified diagrams of side views of a patient coordinate space including a medical instrument mounted on an insertion assembly according to some embodiments.
Figure 3B:
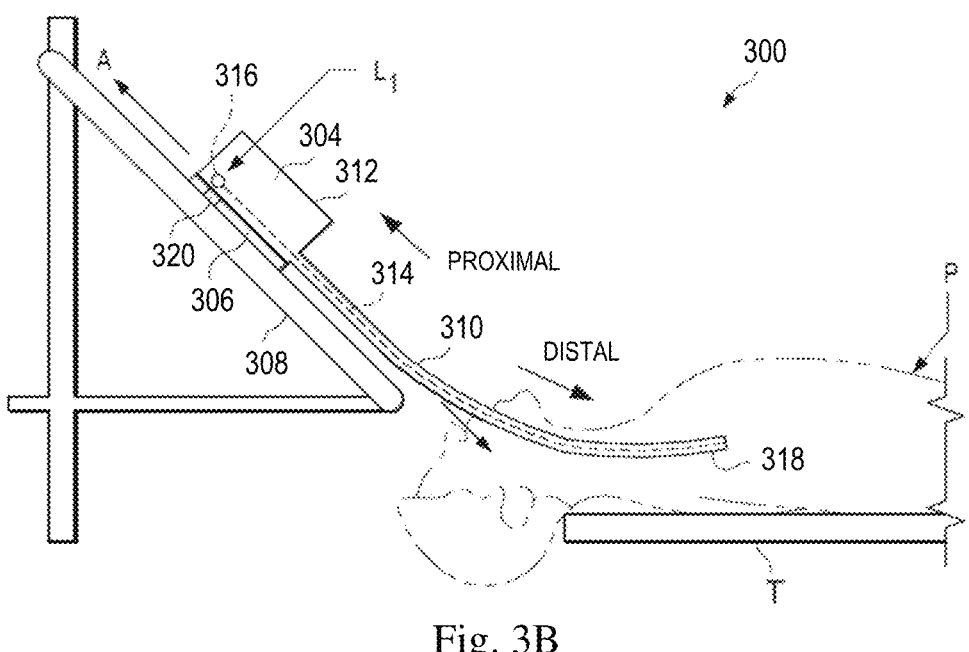

FIGS. 3A and 3B are simplified diagrams of side views of a patient coordinate space including a medical instrument mounted on an insertion assembly according to some embodiments. As shown in FIGS. 3A and 3B, a surgical environment 300 may include a patient P positioned on the patient table T. Patient P may be stationary within the surgical environment 300 in the sense that gross patient movement is limited by sedation, restraint, and/or other means. Cyclic anatomic motion, including respiration and cardiac motion, of patient P may continue. Within surgical environment 300, a medical instrument 304 is used to perform a medical procedure which may include, for example, surgery, biopsy, ablation, illumination, irrigation, suction, or electroporation. The medical instrument 304 may also be used to perform other types of procedures, such as a registration procedure to associate the position, orientation, and/or pose data captured by the sensor system 108 to a desired (e.g., anatomical or system) reference frame. The medical instrument 304 may be, for example, the medical instrument 104. In some examples, the medical instrument 304 may include an elongate device 310 (e.g., a catheter) coupled to an instrument body 312. Elongate device 310 includes one or more channels sized and shaped to receive a medical tool.

Elongate device 310 may also include one or more sensors (e.g., components of the sensor system 108). In some examples, a shape sensor 314 may be fixed at a proximal point 316 on the instrument body 312. The proximal point 316 of the shape sensor 314 may be movable with the instrument body 312, and the location of the proximal point 316 with respect to a desired reference frame may be known (e.g., via a tracking sensor or other tracking device). The shape sensor 314 may measure a shape from the proximal point 316 to another point, such as a distal end 318 of the elongate device 310. The shape sensor 314 may be aligned with the elongate device 310 (e.g., provided within an interior channel or mounted externally). In some examples, the shape sensor 314 may optical fibers used to generate shape information for the elongate device 310.

In some examples, position sensors (e.g., EM sensors) may be incorporated into the medical instrument 304. A series of position sensors may be positioned along the flexible elongate device 310 and used for shape sensing. Position sensors may be used alternatively to the shape sensor 314 or with the shape sensor 314, such as to improve the accuracy of shape sensing or to verify shape information.

Elongate device 310 may house cables, linkages, or other steering controls that extend between the instrument body 312 and the distal end 318 to controllably bend the distal end 318. In some examples, at least four cables are used to provide independent up-down steering to control a pitch of distal end 318 and left-right steering to control a yaw of distal end 318. The instrument body 312 may include drive inputs that removably couple to and receive power from drive elements, such as actuators, of a manipulator assembly.

The instrument body 312 may be coupled to an instrument carriage 306. The instrument carriage 306 may be mounted to an insertion stage 308 that is fixed within the surgical environment 300. Alternatively, the insertion stage 308 may be movable but have a known location (e.g., via a tracking sensor or other tracking device) within surgical environment 300. Instrument carriage 306 may be a component of a manipulator assembly (e.g., manipulator assembly 102) that couples to the medical instrument 304 to control insertion motion (e.g., motion along an insertion axis A) and/or motion of the distal end 318 of the elongate device 310 in multiple directions, such as yaw, pitch, and/or roll. The instrument carriage 306 or insertion stage 308 may include actuators, such as servomotors, that control motion of instrument carriage 306 along the insertion stage 308.

A sensor device 320, which may be a component of the sensor system 108, may provide information about the position of the instrument body 312 as it moves relative to the insertion stage 308 along the insertion axis A. The sensor device 320 may include one or more resolvers, encoders, potentiometers, and/or other sensors that measure the rotation and/or orientation of the actuators controlling the motion of the instrument carriage 306, thus indicating the motion of the instrument body 312. In some embodiments, the insertion stage 308 has a linear track as shown in FIGS. 3A and 3B. In some embodiments, the insertion stage 308 may have curved track or have a combination of curved and linear track sections.

FIG. 3A shows the instrument body 312 and the instrument carriage 306 in a retracted position along the insertion stage 308. In this retracted position, the proximal point 316 is at a position L0 on the insertion axis A. The location of the proximal point 316 may be set to a zero value and/or other reference value to provide a base reference (e.g., corresponding to the origin of a desired reference frame) to describe the position of the instrument carriage 306 along the insertion stage 308. In the retracted position, the distal end 318 of the elongate device 310 may be positioned just inside an entry orifice of patient P. Also in the retracted position, the data captured by the sensor device 320 may be set to a zero value and/or other reference value (e.g., I=0). In FIG. 3B, the instrument body 312 and the instrument carriage 306 have advanced along the linear track of insertion stage 308, and the distal end 318 of the elongate device 310 has advanced into patient P. In this advanced position, the proximal point 316 is at a position L1 on the insertion axis A. In some examples, the rotation and/or orientation of the actuators measured by the sensor device 320 indicating movement of the instrument carriage 306 along the insertion stage 308 and/or one or more position sensors associated with instrument carriage 306 and/or the insertion stage 308 may be used to determine the position L1 of the proximal point 316 relative to the position L0. In some examples, the position L1 may further be used as an indicator of the distance or insertion depth to which the distal end 318 of the elongate device 310 is inserted into the passageway(s) of the anatomy of patient P.

Figures 4, 5:
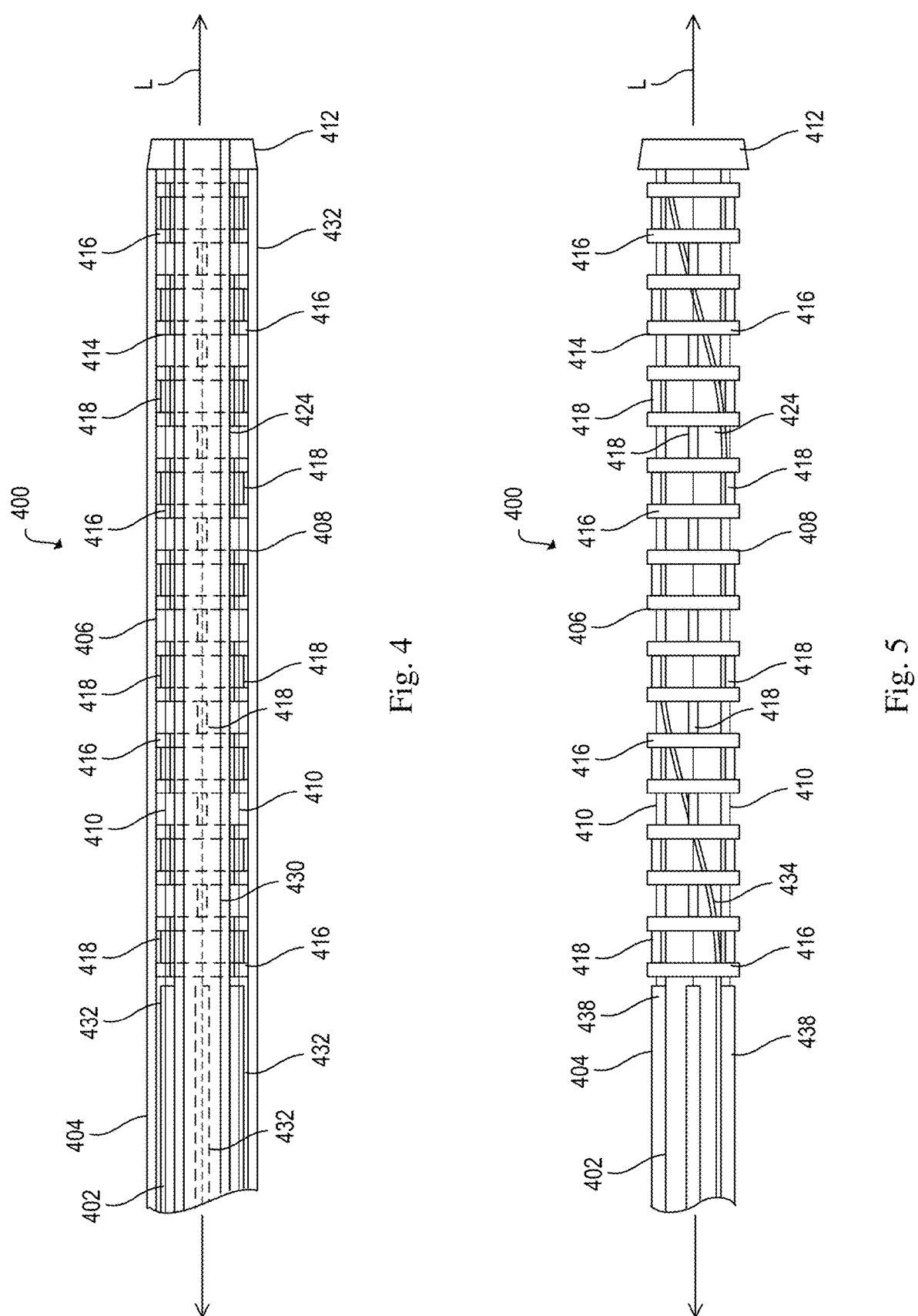
FIG. 4 is a simplified diagrammatic cross-sectional view of a portion of a flexible elongate device according to some embodiments.
FIG. 5 is a simplified diagrammatic view of a portion of a flexible elongate device according to some embodiments.
Figures 6A, 6B, 6C, 6D:
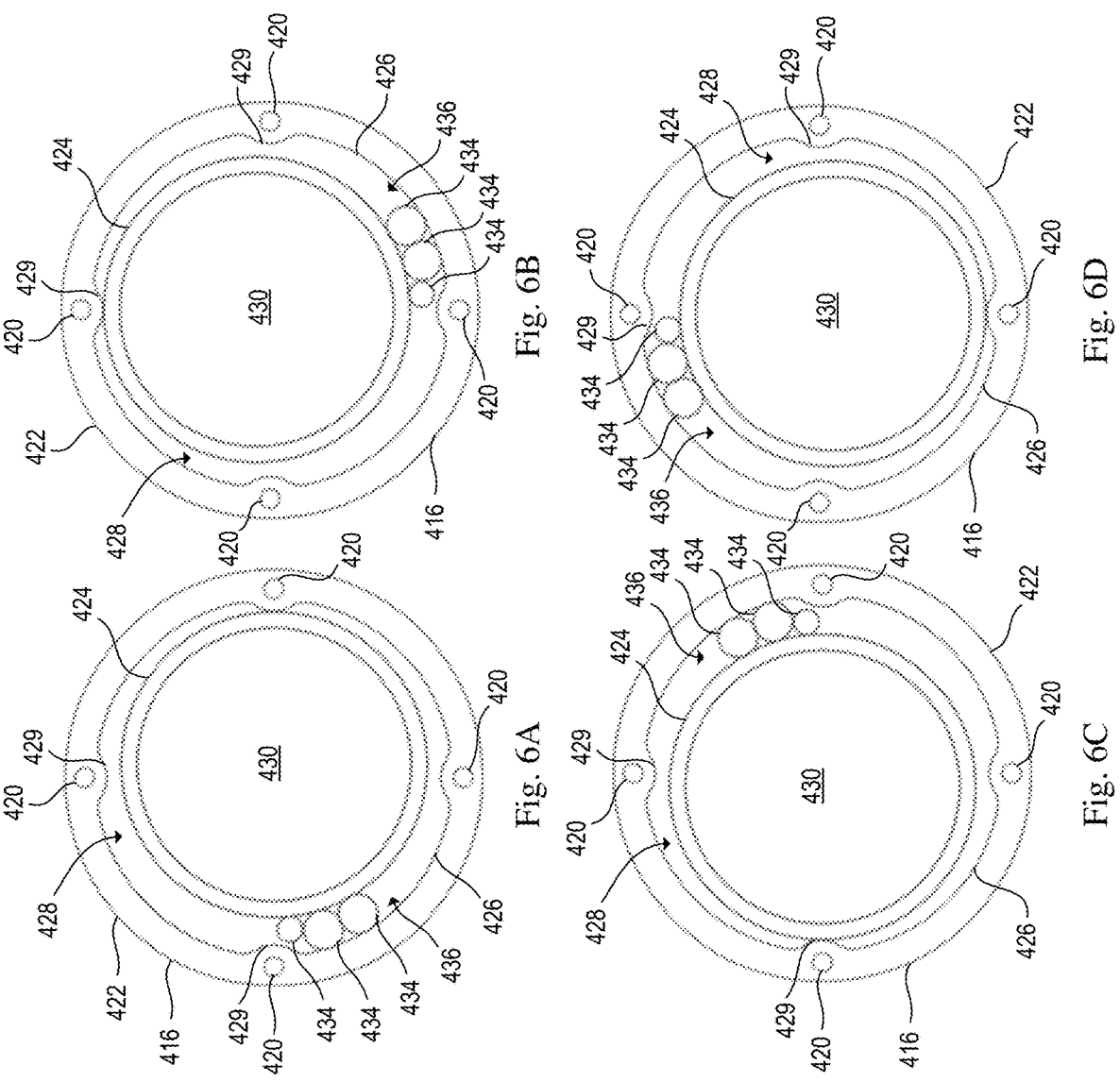
FIGS. 6A-6D are diagrammatic cross-sectional views of a support segment of an example axial support structure having a body member and component lines extending therethrough showing the body member and component lines in sequential positions according to some embodiments.

FIGS. 4 and 5 are simplified diagrams of a flexible elongate device 400 according to some embodiments. According to some embodiments consistent with FIGS. 1-3, the flexible elongate device 400 may correspond to the elongate device 202 of the medical instrument system 200.

As shown in the simplified cross-sectional diagram of FIG. 4, the flexible elongate device 400 can include a flexible body 402 extending from a proximal section 404 to a distal section 406. It will be understood that the flexible body 402, including the proximal and distal sections 404, 406 thereof, can have any desired length. The flexible elongate device 400 includes an articulable body portion 408, which in some examples can be located in or form the distal section 406 thereof.

To control articulation of the articulable body portion 408, a plurality of pull wires 410 extend along the flexible body 402 and connect to a control structure 412 (e.g., a control ring) at a distal end thereof. The pull wires 410 may connect to the control structure 412 by any suitable method. For example, the pull wires 410 can connect to the control structure 412 by welding to the exterior of the control structure 412 and/or by extending within apertures of the control structure 412. The pull wires 410 are spaced circumferentially about the flexible body 402. In some embodiments the pull wires 410 are spaced radially in an even spacing, while in other embodiments the pull wires 410 are spaced radially in an uneven spacing.

As shown, the flexible elongate device 400 further includes an axial support structure 414 that receives the pull wires 410 and is configured to bend in response to actuation forces being applied to the pull wires 410. To maneuver the flexible elongate device 400, unequal actuation forces are applied to the pull wires 410, such that the articulable body portion 408 bends in the direction defined by the net torque proportional to the bending stiffness of the distal section 406/articulable body portion 408. The axial support structure 414 supports the articulable body portion 408 against axial loads generated by the actuation forces applied to the pull wires 410. In particular, the axial support structure 414 may prevent or reduce distortion, compression, and/or collapse of the articulable body portion 408 under axial loads.

The axial support structure 414 includes support segments 416 and tubular struts 418. As shown, the support segments 416 extend transversely relative to a longitudinal axis L of the flexible elongate device 400 and are longitudinally spaced along the articulable body portion 408. The axial support structure 414 can include any desired number of support segments 416 to provide an articulable body portion 408 of sufficient length. The tubular struts 418 extend generally parallel to the longitudinal axis L of the flexible elongate device and are disposed between adjacent support segments 416.

To allow the axial support structure 414 to bend, longitudinally adjacent tubular struts 418 (e.g., tubular struts 418 having a support segment 416 disposed therebetween) are circumferentially offset relative to one another. This configuration imparts axial stiffness to the axial support structure 414, while allowing adjacent portions of the axial support structure to bend in different directions (e.g., along an axis lateral to the neutral axis relative to the tubular struts 418).

In some examples, the tubular struts 418 disposed between adjacent support segments 416 includes a pair of tubular struts 418 that are disposed on opposite sides of the adjacent support segments 416. Further, longitudinally adjacent pairs of tubular struts 418 (e.g., pairs of tubular struts 418 separated by a support segment 416) can be circumferentially offset relative to one another by 90 degrees, such that every other section of the axial support structure 414 can bend along the same axis and the axial support structure 414 can bend along two axes (e.g., pitch and yaw). In other examples, longitudinally adjacent pairs of tubular struts 418 can be circumferentially offset relative to one another by 120 degrees for a three pull wire 410 configuration. Other suitable configurations for additional pull wires 410 can also be utilized.

Each support segment 416 receives the pull wires 410 therethrough. In some examples, the support segments 416 include pull wire openings 420 extending longitudinally therethrough corresponding to the number and circumferential position of the pull wires 410. The pull wire openings 420 can take any suitable form. For example, the pull wire openings 420 can be a apertures as shown in solid lines in FIGS. 6A-6D.

Figure 7:
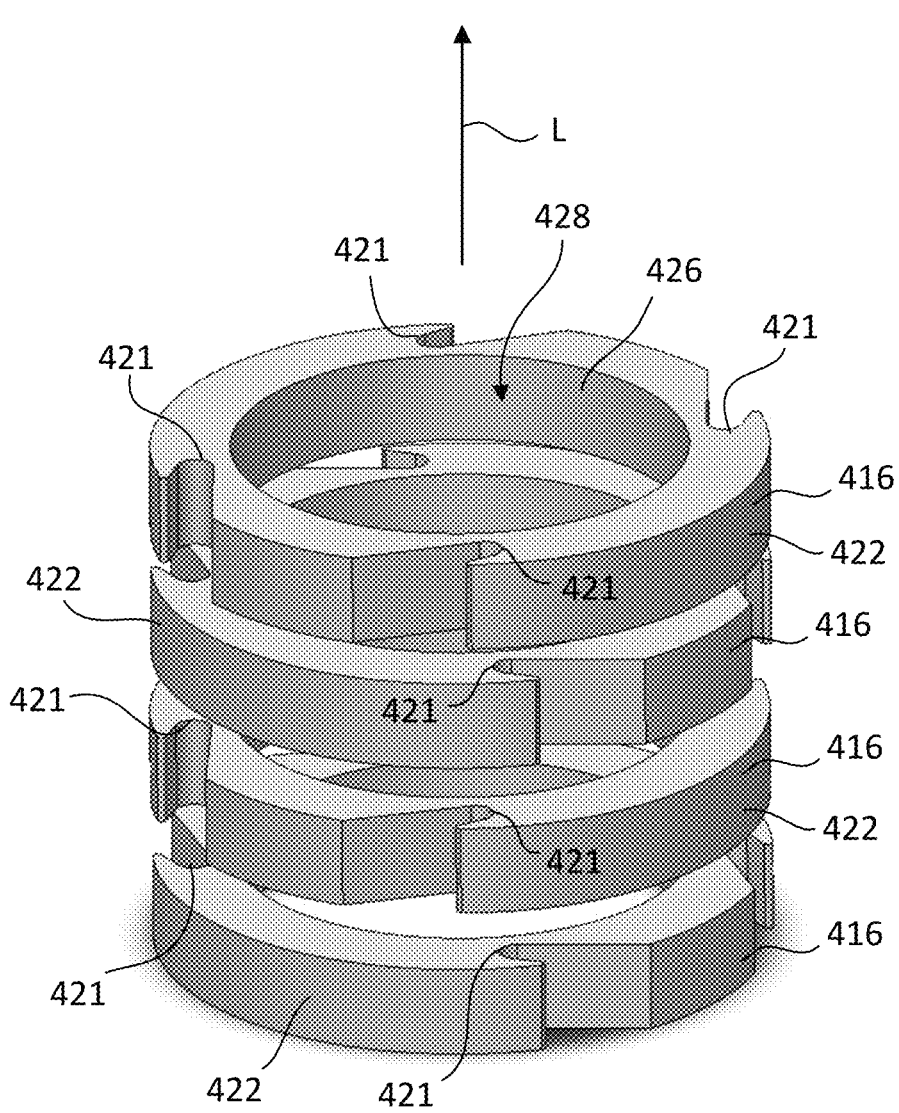
FIG. 7 is a diagrammatic perspective view of support segments of an example axial support structure according to some embodiments.

In another example, the pull wire openings 420 can be grooves 421 as shown in FIG. 7 that open through an outer surface 422 of the support segments 416. The grooves 421 may have a hook shape that allows the pull wires 410 to be side loaded into the pull wire grooves 421, as compared to being threaded through an aperture. In some examples, the grooves 421 are open through an inner surface 426 of the support segments 416 rather than the outer surface 422. In some examples, the orientation of the groove pull wire openings 421 can be switched from one support segment 416 to the next to capture the pull wire (not shown) therein, such that the grooves 421 extend in a sequential clockwise, counterclockwise pattern between adjacent support segments 416 as shown in FIG. 7. The groove configuration can reduce assembly times and can be advantageous for pull wire materials that may catch while being threaded through an aperture, such as multifilament or fibrous material.

These configurations may provide structure of the support segments 416 both radially inward and radially outward of the respective pull wire 410 to engage and support the pull wire 410 in both active and passive articulation movements.

Each tubular strut 418 in the axial support structure 414 aligns with the adjacent support segments 416 to receive one of the pull wires 410 therethrough.

In the above-described example having tubular struts 418 with 90 degree offsets, the flexible elongate device 400 has four pull wires 410, with two of the pull wires 410 received within every other pair of tubular struts 418 and the other two of the pull wires 410 received within the opposite pairs of tubular struts 418 to control articulation of the articulable body portion 408 along pitch and yaw axes. As a result, in this and other examples, one, two, or more pull wires 410 may extend between adjacent support segments 416 that are not received within one of the tubular struts 418.

In some embodiments, the flexible elongate device 400 may include 2, 3, 4, 5, 6, or more pull wires 410 to articulate the articulable body portion 408. More than four pull wires 410 provide articulation along pitch and yaw axes in addition to providing additional functions or compounded geometry (e.g., S curvature). The tubular struts 418 can be distributed along the axial support structure 414 to accommodate desired articulation bending and/or patterns.

In some examples, the support segments 416 and the tubular struts 418 are separate components. With the above configuration having the pull wires 410 extending through the support segments 416 and the tubular struts 418, the pull wires 410 effectively ensure that the support segments 416 and tubular struts 418 stay in position relative to one another and provide an axial support structure 414 with reliable bending and axial stiffness.

As shown in FIGS. 4 and 6A-6D, the flexible elongate device 400 can include an inner body member 424 that extends through the axial support structure 414. In this example, the support segments 416 can have an interior surface 426 defining a central aperture 428 sized to receive the inner body member 424 therethrough and the tubular struts 418 are arranged circumferentially around the central aperture 428. For example, the support segments 416 can have a ring shape. Other examples, such as those without a central aperture, can be suitable for other steerable tools, e.g., a heart mapping catheter, or non-medical steerable tools, e.g., a borescope or plumber's scope.

Depending on manufacturing requirements or desired configurations, the support segments 416 can include protrusions 429 that extend into the central aperture 428 to accommodate the pull wire openings 420, while also minimizing the depth of the adjacent areas of the support segments 416. Alternatively, the support segments 416 could have a uniform thickness sufficient to accommodate the pull wire openings 420.

In some examples, the inner body member 424 can define or include a lumen 430 extending through the flexible body 402. The lumen 430 can provide a delivery channel for a medical tool, such as an endoscope, biopsy needle, endobronchial ultrasound (EBUS) probe, ablation tool, electroporation tool, chemical delivery tool, and/or the like, to be inserted through the flexible body 402.

The flexible elongate device 400 may also include an outer jacket 432 disposed over the inner body member 424 and the axial support structure 414 to at least partially define an exterior surface of the flexible body 402. The outer jacket 432 can be made from any suitable polymer, metal, or composite material, including polyurethane of various durometers, e.g., high durometer polyurethanes, or a stiffer material having a hardness or durometer higher than polyurethane. Suitable examples can include nylon, polyetheretherketone (PEEK), and so forth. The outer jacket 432 can be deposited onto the inner body member 424 and the axial support structure 414 by any suitable method, including lamination, extrusion, etc.

As shown in FIG. 5, the flexible elongate device 400 may include one or more component lines 434 extending along the length thereof. The component lines may include components of the flexible elongate device 400 (e.g., a shape sensor) or portions of components located more distally (e.g., wiring for a sensor or other electronic device, illumination fiber for an imaging device, fluid tubing, etc.). In examples having multiple component lines 434, the lines 434 can run separately along the flexible elongate device 400 or be bundled together. The component lines 434 can have any desired functionality. In some examples, the flexible elongate device 400 may include one or more of: a shape sensor (e.g., fiber optic shape sensor), an imaging device, a wire, illumination fiber, etc.

In embodiments having the inner body member 424 and support segments 416 having the aperture 428, the component line(s) 434 can extend between the interior surface 426 of the support segments 416 and an exterior surface of the inner body member 424. In one form, the component line(s) 434 extend longitudinally along the flexible body 402 in both the proximal and distal sections 404, 406 in a substantially parallel direction to the pull wires 410.

In another form, the component line(s) 434 have a helical shape within the articulable body portion 408 between the axial support structure 414 and the inner body member 424. With a full circumferential turn, the helical shape advantageously minimizes tension and compression forces imparted on component lines having a more longitudinal positioning due to bending of the articulable body portion 408. In one example, if the component line 434 is or includes a shape sensor in a helical shape, the system (e.g., a control system coupled to the shape sensor) is provided with a volumetric representation of the articulable body portion 408 based on data received from the shape sensor.

In some embodiments, the support segments 416 can be sized so that the central apertures 428 have a diameter greater than an outer diameter of the inner body member 424, such that the component lines) 434 can be disposed at any circumferential location. In other embodiments, the central apertures 428 can be relatively smaller, such that there is only clearance between the inner body member 424 and the central aperture interior surface 426 with the inner body member 424 offset from center. In these embodiments, the inner body member 424 can be offset to a uniform radial/circumferential position relative to the support segments 416 and inner body member 424 to allow the component line(s) 434 to extend longitudinally along the inner body member 424. Alternatively, as shown in FIGS. 6A-6D, the inner body member 424 can have a corkscrew configuration within the articulable body portion 408 and the axial support structure 414, such that portions 436 of the support segment interior surfaces 426 spaced from the inner body member 424 of adjacent support segments 416 are circumferentially offset. The circumferential offset relative to adjacent support segments 416 imparts the helical shape on the component line(s) 434.

The support segments 416 can be made from any suitable material, including low friction materials. In some examples, the support segments 416 can be made from a polymer material, such as polyoxymethylene (POM), also referred to as acetal, or a coated metal.

The tubular struts 418 can be made from any suitable material, including low friction materials. In some examples, the tubular struts 418 can be made from a polymer material, such as polytetrafluoroethylene (PTFE) doped polyimide, or a coated metal. The tubular struts 418 can also have a variety of different suitable forms, including a braided metal, a coil pipe, springs, and so forth.

Although some example axial support structures are described herein, the helical shape of the component line(s) 434 within the axial support structure, as well as the corkscrew configuration of the articulable body portion 408 of the flexible elongate device 402 can be utilized with axial support structures of other configurations. Other example axial support structures are described in U.S. patent application Ser. No. 16/932,196 (filed Jul. 17, 2020), U.S. patent application Ser. No. 16/473,439 (filed Jun. 25, 2019), U.S. patent application Ser. No. 15/685,979 (filed Aug. 24, 2017), and U.S. Provisional Patent Application 62/535,673 (filed Jul. 21, 2017), each of which is hereby incorporated by reference in its entirety.

In any of the above examples, the flexible elongate device 400 can include a plurality of tubes 438 bonded or otherwise coupled to the proximal section 404 thereof. The tubes 438 are aligned with and provide structure for the pull wires 410 to extend through in the proximal section 404. In some examples, the tubes 438 extend longitudinally along the inner body member 424 to support the pull wires 410. For example, the tubes 438 can be bonded to the inner body member 424 by any suitable material, such as an aqueous polyimide, an epoxy, an adhesive (e.g., UV curable), and so forth.

One or more components of the embodiments discussed in this disclosure, such as control system 112, may be implemented in software for execution on one or more processors of a computer system. The software may include code that when executed by the one or more processors, configures the one or more processors to perform various functionalities as discussed herein. The code may be stored in a non-transitory computer readable storage medium (e.g., a memory, magnetic storage, optical storage, solid-state storage, etc.). The computer readable storage medium may be part of a computer readable storage device, such as an electronic circuit, a semiconductor device, a semiconductor memory device, a read only memory (ROM), a flash memory, an erasable programmable read only memory (EPROM); a floppy diskette, a CD-ROM, an optical disk, a hard disk, or other storage device. The code may be downloaded via computer networks such as the Internet, Intranet, etc. for storage on the computer readable storage medium. The code may be executed by any of a wide variety of centralized or distributed data processing architectures. The programmed instructions of the code may be implemented as a number of separate programs or subroutines, or they may be integrated into a number of other aspects of the systems described herein. The components of the computing systems discussed herein may be connected using wired and/or wireless connections. In some examples, the wireless connections may use wireless communication protocols such as Bluetooth, near-field communication (NFC), Infrared Data Association (IrDA), home radio frequency (HomeRF), IEEE 802.11, Digital Enhanced Cordless Telecommunications (DECT), and wireless medical telemetry service (WMTS).

Various general-purpose computer systems may be used to perform one or more processes, methods, or functionalities described herein. Additionally or alternatively, various specialized computer systems may be used to perform one or more processes, methods, or functionalities described herein. In addition, a variety of programming languages may be used to implement one or more of the processes, methods, or functionalities described herein.

While certain embodiments and examples have been described above and shown in the accompanying drawings, it is to be understood that such embodiments and examples are merely illustrative and are not limited to the specific constructions and arrangements shown and described, since various other alternatives, modifications, and equivalents will be appreciated by those with ordinary skill in the art.

What is claimed is:

1. A flexible elongate device comprising:
an elongate body having an articulable body portion; and
an axial support structure within the articulable body portion, the axial support structure comprising:
transverse support segments longitudinally spaced along the articulable body portion, each support segment receiving a plurality of pull wires that control articulation of the articulable body portion;
tubular struts disposed between adjacent support segments, adjacent tubular struts separated by one of the support segments being circumferentially offset relative to one another, each tubular strut receiving a pull wire.

2. The flexible elongate device of claim 1, wherein the tubular struts disposed between the adjacent support segments include a pair of tubular struts disposed on circumferentially opposite sides of the adjacent support segments, such that pull wires received within the pair of tubular struts control articulation of the articulable body portion along an axis.

3. The flexible elongate device of claim 2, wherein adjacent pairs of tubular struts separated by one of the support segments are circumferentially offset relative to one another by 90 degrees, such that pull wires received within the adjacent pairs of tubular struts control articulation of the articulable body portion along pitch and yaw axes.

4. The flexible elongate device of claim 1, wherein adjacent support segments receive at least one pull wire that is not received within one of the tubular struts disposed therebetween.

5. The flexible elongate device of claim 1, further comprising four pull wires, wherein adjacent pairs of tubular struts are circumferentially offset 90 degrees relative to one another allowing pitch and yaw articulation of the articulable body portion.

6. The flexible elongate device of claim 1, further comprising three pull wires, wherein adjacent pairs of tubular struts are circumferentially offset 120 degrees relative to one another allowing articulation of the articulable body portion.

7. The flexible elongate device of claim 1, wherein the support segments define pull wire apertures extending therethrough for the plurality of pull wires.

8. The flexible elongate device of claim 1, wherein the support segments define pull wire grooves extending therethrough for the plurality of pull wires.

9. The flexible elongate device of claim 1, wherein the elongate body comprises an inner body member defining a lumen, and each support segment defines a central aperture that receives the inner body member therethrough.

10. The flexible elongate device of claim 9, further comprising a component line, the component line extending between the inner body member and surfaces of the support segments defining the central apertures thereof.

11. The flexible elongate device of claim 10, wherein the component line extends in a helical shape within the articulable body portion.

12. The flexible elongate device of claim 11, wherein the inner body member has a corkscrew configuration within the articulable body portion, such that portions of the surfaces of the support segments defining the central apertures thereof that are spaced from the inner body member are circumferentially offset in adjacent support segments.

13. The flexible elongate device of claim 11, wherein the component line comprises a shape sensor, the helical shape of the shape sensor providing a volumetric representation of the articulable body portion.

14. The flexible elongate device of claim 10, wherein the component line comprises at least one of a wire or optical fiber.

15. The flexible elongate device of claim 10, wherein the component line comprises a plurality of component lines.

16. The flexible elongate device of claim 1, wherein the tubular struts comprise a polymer material.

17. The flexible elongate device of claim 1, wherein the tubular struts comprise one or more of a coated metal, a braided metal, coil pipes, or springs.

18. The flexible elongate device of claim 1, wherein the support segments comprise a polymer or coated metal.

19. The flexible elongate device of claim 1, wherein the support segments and tubular struts are separate components.

20. The flexible elongate device of claim 1, wherein the elongate body further comprises an outer jacket disposed over the axial support structure.

21. The flexible elongate device of claim 1, wherein the elongate body comprises a proximal section and a distal section, the distal section including the articulable body portion.

22. The flexible elongate device of claim 21, further comprising a plurality of tubes bonded to the proximal section of the elongate body, each of the plurality of tubes configured to receive one of the plurality of pull wires.

23. The flexible elongate device of claim 1, further comprising a control structure coupled to the elongate body distal to the axial support structure, the control structure attached with the plurality of pull wires to control articulation of the articulable body portion.

* * * * *